(12) United States Patent
Stauffer

(10) Patent No.: US 7,091,391 B2
(45) Date of Patent: Aug. 15, 2006

(54) METHANE TO OLEFINS

(76) Inventor: John E. Stauffer, 6 Pecksland Rd., Greenwich, CT (US) 06830

( * ) Notice: Subject to any disclaimer, the term of this patent is extended or adjusted under 35 U.S.C. 154(b) by 517 days.

(21) Appl. No.: 10/391,926

(22) Filed: Mar. 19, 2003

(65) Prior Publication Data

US 2004/0186334 A1  Sep. 23, 2004

(51) Int. Cl.
*C07C 1/00* (2006.01)
(52) U.S. Cl. ........................... 585/642; 585/641
(58) Field of Classification Search ............ 585/641, 585/642
See application file for complete search history.

(56) References Cited

U.S. PATENT DOCUMENTS

| | | | |
|---|---|---|---|
| 5,001,293 A * | 3/1991 | Nubel et al. | 585/408 |
| 5,099,084 A | 3/1992 | Stauffer | |
| 6,680,415 B1 * | 1/2004 | Gulotty et al. | 570/243 |

OTHER PUBLICATIONS

Kirk-Othmer, Encyclopedia of Chemical Technology, 4th ed., vol. 5, p. 1031-1032.

* cited by examiner

*Primary Examiner*—Walter D. Griffin
*Assistant Examiner*—In Suk Bullock
(74) *Attorney, Agent, or Firm*—Young & Basile, P.C.

(57) ABSTRACT

The specification discloses a process for the production of olefins, including ethylene, propylene and butenes, from methane, the process comprising first, second and third reaction steps operated in tandem. In the first reaction step, hydrogen chloride, perchloroethylene and oxygen are reacted in the presence of a catalyst, using methane as a diluent, to yield hexachloroethane and water. In the second reaction step, the hexachoroethane from the first reaction step is reacted with methane to produce methyl chloride, hydrogen chloride and perchloroethylene. In the third reaction step, the methyl chloride from the second reaction step is reacted to give the desired olefins and hydrogen chloride. By recycling the perchloroethylene from the second reaction step and the hydrogen chloride from both the second and third reaction steps to the first reaction step, a balanced process is achieved that is self-sufficient in chlorine values.

8 Claims, 1 Drawing Sheet

METHANE TO OLEFINS

FIELD OF THE INVENTION

The present invention relates to a process for producing olefins, including ethylene, propylene and butenes, from methane; and more particularly to such a process where perchloroethylene, hydrogen chloride and oxygen are reacted in the presence of a catalyst, using methane as a diluent, to yield reaction products comprising hexachloroethane and water, and wherein the hexachloroethane is reacted with methane to produce methyl chloride, hydrogen chloride and perchloroethylene, and wherein the methyl chloride so produced is reacted in a coupling reaction to produce the desired olefins.

BACKGROUND OF THE INVENTION

Olefins, including ethylene, propylene and butenes, are major building blocks in the chemical process industries. These materials are either recovered from refinery streams or produced by cracking naphtha or LPG. Not with standing the success of these processes, there is an incentive to use methane as a raw material because of the large reserves of natural gas throughout the world.

From the prior art (Kirk-Othmer, *Encyclopedia of Chemical Technology*, $4^{th}$ ed., Vol. 5, p. 1031), methyl chloride, when heated to very high temperatures, is known to couple giving ethylene and hydrogen chloride. At somewhat lower temperatures, catalytic reactions involving methyl chloride also produce ethylene and other olefins.

The literature (U.S. Pat. No. 5,099,084) further discloses a process for the chlorination of methane using hydrogen chloride as the source of chlorine. This process, however, is attended by several drawbacks. Not only is methyl chloride produced, but the higher chlorinated methanes, including methylene chloride, chloroform and carbon tetrachloride, are also generated. In addition, when air is employed in the catalytic reaction, a substantial quantity of gases must be vented, thereby complicating emission control problems and related environmental concerns. On the other hand, the use of pure oxygen hinders the reaction due to the formation of hot spots in the catalyst bed.

There consequently exists a need for a process that starts with methane as a raw material and converts it through the formation of methyl chloride into olefins. Such an integrated process must at once be economical to operate and reduce the inefficiencies characterizing conventional processes.

SUMMARY OF THE DISCLOSURE

The specification discloses a largely self-contained process for producing olefins from methane, comprising the following steps operated in tandem:

a first reaction step wherein hydrogen chloride, perchloroethylene and oxygen are reacted in the presence of a catalyst, using methane as a diluent, to yield reaction products comprising hexachloroethane and water;

a second reaction step wherein the hexachloroethane of the first reaction step is reacted with methane to produce methyl chloride, hydrogen chloride and perchloroethylene; and a third reaction step wherein methyl chloride of the second reaction step is reacted to give olefins and hydrogen chloride.

The process is operated in a balanced mode such that the perchloroethylene from the second reaction step is recycled to the first reaction step, and the hydrogen chloride from both the second and third reaction steps is supplied to the first reaction step. In addition, unreacted methane from the second reaction step is returned to the first reaction step where it functions as a diluent.

Per another feature of the process, the catalyst of the first reaction step comprises copper chloride or an admixture of copper chloride and a salt selected from the group consisting of potassium chloride, iron chloride, lead chloride and cesium chloride.

According to another feature of the invention, the first reaction step is carried out at a temperature in the range of from approximately 200° C. to approximately 375° C.

Per still another feature, the second reaction step is carried out at a temperature in the range of from approximately 400° C. to approximately 700° C.

BRIEF DESCRIPTION OF THE DRAWING

The written description herein makes reference to the accompanying drawing.

WRITTEN DESCRIPTION

Figure 1:
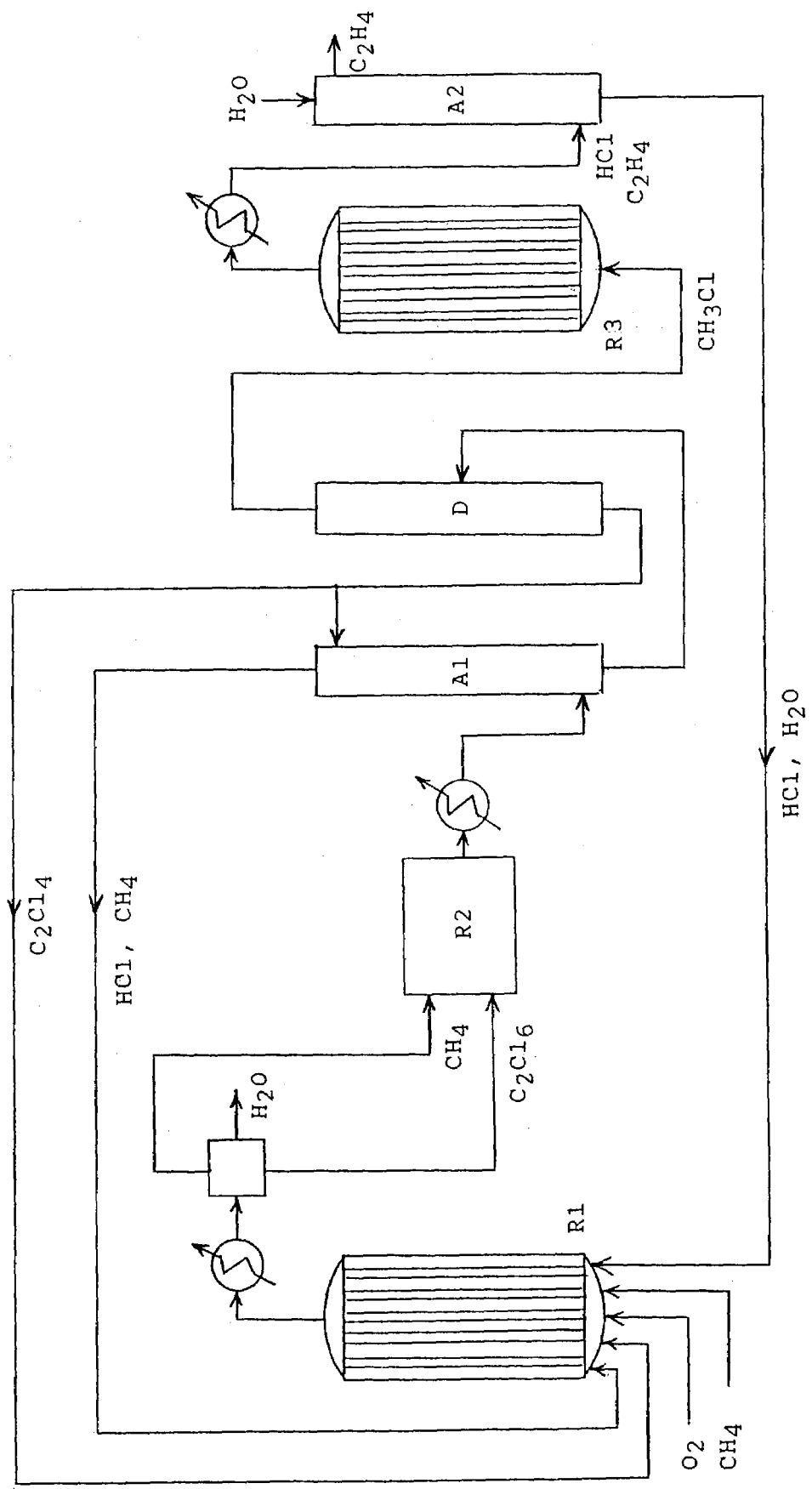
FIG. 1 is a flow diagram of one embodiment of the present invention depicting three reactors, including a first catalytic reactor, a thermal reactor, and a second catalytic reactor as well as a first absorption column, a distillation column and a second absorption column.

Referring now to FIG. 1 wherein the process of this invention is shown diagrammatically, the present invention will be seen to comprise essentially a method for producing an olefin, in this case ethylene ($C_2H_4$) from methane ($CH_4$) and oxygen ($O_2$). More particularly, the process of this invention comprises a first reaction step, wherein hydrogen chloride (HCl), perchloroethylene ($C_2Cl_4$) and oxygen are reacted in the presence of a catalyst, using methane as a diluent, to give reaction products hexachloroethane ($C_2Cl_6$) and water ($H_2O$). In a second reaction step, the hexachloroethane from the first reaction step is reacted with methane to produce methyl chloride ($CH_3Cl$), hydrogen chloride and perchloroethylene. The perchloroethylene, hydrogen chloride and unreacted methane are returned to the first reaction step. In a third reaction step, the methyl chloride from the second reaction step is reacted to produce ethylene and hydrogen chloride. The hydrogen chloride so produced is supplied to the first reaction step after separating it from the ethylene product.

These first, second and third reaction steps are represented, respectively, by the following equations 1, 2, and 3.

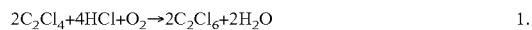

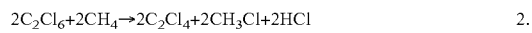

The foregoing equations may be combined, as the following equation 4, to represent the overall reaction of the present invention.

According to the first reaction step, shown in equation 1, perchloroethylene is reacted with hydrogen chloride and oxygen in an oxychlorination reaction to yield hexachloroethane and water. This reaction is carried out in the presence of a catalyst comprising copper chloride or an admixture of copper chloride and a metal chloride selected from the group potassium chloride, iron chloride, lead chloride and cesium chloride. The catalyst may be deposited on an inert support for use in a shell and tube reactor (R1) as shown in FIG. 1 or a fluidized bed reactor. Alternatively, the catalyst may be in the form of a molten salt. The temperature for this first reaction step is in the range of approximately 200° C. to approximately 375° C.

The oxychlorination reaction is highly exothermic in nature. As a result, the heat given off by the reaction tends to cause troublesome hot spots in the catalyst, especially if pure oxygen is used. On the other hand, should air be employed as a diluent to control these hot spots, a substantial quantity of gases must be vented from the system, thus complicating emission control problems. The present invention circumvents this difficulty by carrying out the first reaction step in the presence of methane which under the conditions of the reaction is inert and serves to remove heat from the catalyst surface. Substantially all of the hydrogen chloride and oxygen are consumed in the first reaction step so that methane in the reactor effluent is free from these reactants.

In the second reaction step, methane is reacted with the hexachloroethane product of the first reaction step to produce methyl chloride, hydrogen chloride and perchloroethylene. This second reaction step is carried out in a thermal reactor (R2) in the range of approximately 400° C. to approximately 700° C. The mechanism for the chlorination of methane is believed to be a series of free-radical reactions. First, chlorine is released from the hexachloroethane and then chlorine molecules form free radicals which start the chain reaction.

Normally, higher chlorinated methane compounds, including methylene chloride, chloroform and carbon tetrachloride, would be produced in the second reaction step along with methyl chloride. In order to suppress the formation of these higher chlorinated methanes an excess of methane is fed to the reactor. Thus, the exit gases from the thermal reactor contain a substantial volume of methane in addition to the reaction products. This methane, however, need not be separated from the hydrogen chloride in a costly operation because, as noted already, methane is employed as a diluent in the first reaction step.

The methyl chloride from the second reaction step is recovered by scrubbing the cooled effluent gases from the thermal reactor with perchloroethylene in an absorption column (A1). The absorbed methyl chloride is then separated from the perchloroethylene scrubbing solution in a distillation column (D). This recovered methyl chloride is the feed for the third reaction step.

Although the prior art indicates that methyl chloride will react to give ethylene and hydrogen chlorine in a thermal reaction, the preferred approach is to use a catalytic reaction. This choice has two major advantages. Not only are significantly lower operating temperatures possible, but the catalyst can be tailored to provide higher yields of the desired olefin. The process of the present invention produces not only ethylene but also homologues of this olefin. Thus, the production of propylene can be represented by equation 5 as follows.

$$3CH_3Cl \rightarrow C_3H_6 + 3HCl \qquad 5.$$

In addition to catalyst selectivity, the reaction conditions can be used to control the ratio of olefins produced within certain limits.

A probable mechanism can be determined for the catalytic conversion of methyl chloride to ethylene and hydrogen chloride. It is known that methyl chloride can be hydrolyzed to methyl alcohol and hydrogen chloride. Furthermore methyl alcohol has been shown to react to produce olefins and water. These reactions are illustrated by the following equations 6 and 7.

$$2CH_3Cl + 2H_2O \rightarrow 2CH_3OH + 2HCl \qquad 6.$$

$$2CH_3OH \rightarrow C_2H_4 + 2H_2O \qquad 7.$$

Combining these two equations gives equation 3 above. The water required for equation 6 is supplied by the reaction of equation 7. Most likely there is enough moisture present in the feed gas to initiate these reactions.

Both equations 6 and 7 represent catalytic reactions. The hydrolysis reaction of equation 6 is catalyzed by salts of copper, zinc and bismuth and by alumina gel. In many reaction systems, silica-alumina catalysts provide results similar to those obtained by pure alumina. The dehydration reaction of equation 7 is catalyzed by silicon-aluminum-phosphorus oxide at a pressure between 1 and 5 bars and a temperature in the range of 350° C. to 500° C. In addition silica-alumina based zeolites have been shown to promote dehydration.

Based on the above data, the catalyst of choice for the third reaction step is a silica-alumina catalyst alone or modified with other elements. This reaction is preferably carried out in a shell and tube reactor (R3) at a temperature in the range of about 350° C. to about 500° C. The effluent from the reactor is cooled and then passed to an absorption tower (A2) where hydrogen chloride is separated from the olefins product.

In summary, the unique benefits of the present invention are derived in large part by employing an excess of methane in the second reaction step for the chlorination of methane and by using methane as a diluent in the first reaction step for the oxychlorination of perchloroethylene. These two features are neatly dovetailed into a unified process, as shown in FIG. 1, by circulating methane in a loop between the first and second reaction steps.

Of course, the foregoing is merely illustrative of the present invention. Those persons of ordinary skill in the art will appreciate that many additions and modifications to the present invention, as set out in this disclosure, are possible without departing from the spirit and broader aspects of this invention as defined in the claims herein appended.

The invention in which exclusive property or privilege is claimed is defined as follows:

1. A process for producing olefins, including ethylene, propylene and butenes, from methane, comprising the following steps, operated in tandem:

a first reaction step wherein hydrogen chloride, perchloroethylene and oxygen are reacted in the presence of a catalyst, using methane as a diluent, to yield products hexachloroethane and water, a second reaction step wherein the hexachloroethane of the first reaction step is reacted with an excess of methane to produce reaction products comprising methyl chloride, hydrogen chloride and perchloroethylene;

a third reaction step wherein methyl chloride of the second reaction step is reacted to give olefins, including ethylene, propylene and butenes, and hydrogen chloride; and wherein the perchloroethylene and untreated methane of the second reaction step and the hydrogen chloride from both the second and third reaction steps are returned to the first reaction step.

2. The process of claim 1, wherein the catalyst of the first reaction step comprises copper chloride.

3. The process of claim 1, wherein the catalyst of the first reaction step comprises an admixture of copper chloride and a salt selected from the group consisting of potassium chloride, iron chloride, lead chloride and cesium chloride.

4. The process of claim 1, wherein the first reaction step is carried out at a temperature in the range of approximately 200° C. to approximately 375° C.

5. The process of claim 1, wherein the second reaction step is carried out at a temperature in the range of approximately 400° C. to approximately 700° C.

6. The process of claim 1, wherein the third reaction step is carried out in the presence of a catalyst.

7. The process of claim 6, wherein the catalyst used in the third reaction step is a silica-alumina catalyst.

8. The process of claim 6, wherein the third reaction step is carried out at a temperature in the range of approximately 350° C. to approximately 500° C.

* * * * *